US012605245B2

(12) United States Patent (10) Patent No.: US 12,605,245 B2
Peterson et al. (45) Date of Patent: Apr. 21, 2026

(54) BALLOON EXPANDABLE STENT WITH SYMMETRICAL CRIMPED CONFIGURATION FOR TRANSCATHETER IMPLANTATION OF A CARDIAC VALVE PROSTHESIS

(71) Applicant: MEDTRONIC, INC., Minneapolis, MN (US)

(72) Inventors: Justin Peterson, Santa Rosa, CA (US); Stuart Kari, Windsor, CA (US); Shahnaz Javani, Santa Rosa, CA (US); Genevieve Farrar, Novato, CA (US); Syed Askari, San Jose, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 587 days.

(21) Appl. No.: 18/040,216

(22) PCT Filed: Aug. 3, 2021

(86) PCT No.: PCT/US2021/044270
§ 371 (c)(1),
(2) Date: Feb. 1, 2023

(87) PCT Pub. No.: WO2022/031650
PCT Pub. Date: Feb. 10, 2022

(65) Prior Publication Data
US 2023/0263623 A1 Aug. 24, 2023

Related U.S. Application Data

(60) Provisional application No. 63/060,378, filed on Aug. 3, 2020.

(51) Int. Cl.
*A61F 2/24* (2006.01)
*A61F 2/915* (2013.01)

(52) U.S. Cl.
CPC .............. *A61F 2/2418* (2013.01); *A61F 2/24* (2013.01); *A61F 2/2412* (2013.01); *A61F 2/915* (2013.01);
(Continued)

(58) Field of Classification Search
CPC ............ A61F 2/2418; A61F 2250/0036; A61F 2250/0096–0098
See application file for complete search history.

(56) References Cited

U.S. PATENT DOCUMENTS 5,330,500 A 7/1994 Song
5,411,552 A 5/1995 Andersen et al.
(Continued)

FOREIGN PATENT DOCUMENTS

WO 2003011195 A2 2/2003
WO 20060127765 A1 11/2006
(Continued)

OTHER PUBLICATIONS

International Search Report issued Nov. 23, 2021 in Intl Appl. No. PCT/US2021/044270.

*Primary Examiner* — Rebecca S Preston
(74) *Attorney, Agent, or Firm* — MEDLER FERRO WOODHOUSE & MILLS PLLC

(57) ABSTRACT

A transcatheter valve prosthesis includes a stent and a prosthetic valve. The prosthetic valve is configured to substantially block blood flow in one direction to regulate blood flow through a central lumen of the stent. The stent includes an inflow portion, an outflow portion, and a transition portion extending between the inflow portion and the outflow portion. The transition portion includes a plurality of axial frame members extending between the inflow portion and the outflow portion. Each axial frame member extends in an axial direction from a crown of the inflow portion to
(Continued)

at least a crown of the outflow portion. Each axial frame member has a first end adjacent to the crown of the inflow portion, the first end having a reduced width relative to a width of a length of the axial frame member between the first end and the crown of the outflow portion.

20 Claims, 11 Drawing Sheets

(52) U.S. Cl.
CPC ................. *A61F 2002/9155* (2013.01); *A61F 2220/0075* (2013.01); *A61F 2250/0036* (2013.01); *A61F 2250/0096* (2013.01); *A61F 2250/0098* (2013.01)

(56) References Cited

U.S. PATENT DOCUMENTS

| | | | |
|---|---|---|---|
| 5,840,081 | A | 11/1998 | Andersen et al. |
| 5,931,969 | A | 8/1999 | Carpentier et al. |
| 6,168,614 | B1 | 1/2001 | Andersen et al. |
| 6,210,957 | B1 | 4/2001 | Carpentier et al. |
| 6,214,054 | B1 | 4/2001 | Cunanan et al. |
| 6,458,153 | B1 | 10/2002 | Bailey et al. |
| 6,547,827 | B2 | 4/2003 | Carpentier et al. |
| 6,561,970 | B1 | 5/2003 | Carpentier et al. |
| 6,582,462 | B1 | 6/2003 | Andersen et al. |
| 6,730,118 | B2 | 5/2004 | Spenser et al. |
| 6,830,584 | B1 | 12/2004 | Sequin |
| 6,893,460 | B2 | 5/2005 | Spenser et al. |
| 6,908,481 | B2 | 6/2005 | Cribier |
| 7,018,406 | B2 | 3/2006 | Seguin et al. |
| 7,198,646 | B2 | 4/2007 | Figulla et al. |
| 7,201,772 | B2 | 4/2007 | Schwammenthal et al. |
| 7,214,344 | B2 | 5/2007 | Carpentier et al. |
| 7,252,682 | B2 | 8/2007 | Seguin |
| 7,329,278 | B2 | 2/2008 | Seguin et al. |
| 7,393,360 | B2 | 7/2008 | Spenser et al. |
| 7,429,269 | B2 | 9/2008 | Schwammenthal et al. |
| 7,442,204 | B2 | 10/2008 | Schwammenthal et al. |
| RE40,570 | E | 11/2008 | Carpentier et al. |
| 7,470,285 | B2 | 12/2008 | Nugent et al. |
| 7,510,575 | B2 | 3/2009 | Spenser et al. |
| 7,530,253 | B2 | 5/2009 | Spenser et al. |
| 7,585,321 | B2 | 9/2009 | Cribier |
| 7,618,446 | B2 | 11/2009 | Andersen et al. |
| 7,682,390 | B2 | 3/2010 | Seguin |
| 7,780,723 | B2 | 8/2010 | Taylor |
| 7,780,726 | B2 | 8/2010 | Seguin |
| 7,789,909 | B2 | 9/2010 | Andersen et al. |
| 7,846,203 | B2 | 12/2010 | Cribier |
| 7,993,394 | B2 | 8/2011 | Hariton et al. |
| 8,163,011 | B2 | 4/2012 | Rankin |
| 8,236,045 | B2 | 8/2012 | Benichou et al. |
| 9,089,422 | B2 | 7/2015 | Ryan et al. |
| 9,901,447 | B2 | 2/2018 | Braido et al. |
| 9,943,407 | B2 | 4/2018 | Tuval et al. |
| 10,058,420 | B2 | 8/2018 | Levi |
| 2006/0178740 | A1 | 8/2006 | Stacchino et al. |
| 2006/0259137 | A1 | 11/2006 | Artof et al. |
| 2007/0078510 | A1 | 4/2007 | Ryan |
| 2007/0270944 | A1 | 11/2007 | Bergheim et al. |
| 2008/0154355 | A1 | 6/2008 | Benichou et al. |
| 2009/0192591 | A1 | 7/2009 | Ryan et al. |
| 2009/0287299 | A1 | 11/2009 | Tabor et al. |
| 2010/0268332 | A1 | 10/2010 | Tuval et al. |
| 2011/0015729 | A1 | 1/2011 | Jimenez et al. |
| 2011/0166636 | A1 | 7/2011 | Rowe |
| 2011/0264196 | A1 | 10/2011 | Savage et al. |
| 2011/0301700 | A1 | 12/2011 | Fish et al. |
| 2011/0313515 | A1 | 12/2011 | Quadri et al. |
| 2012/0053681 | A1 | 3/2012 | Aikhatib et al. |
| 2012/0071969 | A1 | 3/2012 | Li et al. |
| 2012/0078356 | A1 | 3/2012 | Fish et al. |
| 2012/0123529 | A1 | 5/2012 | Levi et al. |
| 2013/0023984 | A1 | 1/2013 | Conklin |
| 2013/0150956 | A1 | 6/2013 | Yohanan et al. |
| 2014/0018915 | A1* | 1/2014 | Biadillah .............. A61F 2/2418 623/2.17 |
| 2014/0277389 | A1 | 9/2014 | Braido et al. |
| 2015/0018944 | A1 | 1/2015 | O'Connell et al. |
| 2015/0066141 | A1 | 3/2015 | Braido et al. |
| 2015/0230923 | A1* | 8/2015 | Levi ..................... A61F 2/2418 623/2.36 |
| 2016/0296328 | A1 | 10/2016 | Tabor et al. |
| 2017/0042673 | A1* | 2/2017 | Vietmeier ............ A61F 2/2418 |
| 2018/0029634 | A1 | 2/2018 | Toyama |
| 2021/0275298 | A1* | 9/2021 | Peterson .............. A61F 2/9522 |

FOREIGN PATENT DOCUMENTS

| | | | |
|---|---|---|---|
| WO | 2008150529 | A1 | 12/2008 |
| WO | 201232187 | A1 | 3/2012 |
| WO | 2015126711 | A1 | 8/2015 |

* cited by examiner

116

102

160

106

BALLOON EXPANDABLE STENT WITH SYMMETRICAL CRIMPED CONFIGURATION FOR TRANSCATHETER IMPLANTATION OF A CARDIAC VALVE PROSTHESIS

FIELD OF THE INVENTION

The present invention relates to expandable transcatheter valve prostheses that are radially expandable.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding, mechanically-expandable, or balloon-expandable stent structures with valve leaflets attached to the interior of the stent structure. The prosthetic valve can be reduced in diameter, by collapsing or crimping the stent structure. For example, the stent structure can be crimped onto a balloon catheter or a crimped stent structure can be contained within a sheath component of a delivery catheter, and advanced through the venous or arterial vasculature. Once the prosthetic valve is positioned at the treatment site, for instance within an incompetent native valve, the stent structure may be self, mechanically or balloon expanded to hold the prosthetic valve firmly in place.

Although transcatheter delivery methods have provided safer and less invasive methods for replacing a defective heart valve, complications may arise including vessel trauma due to percutaneous delivery within highly curved anatomy and/or due to a large delivery profile of the prosthesis, inaccurate placement of the valve prosthesis, conduction disturbances, coronary artery obstruction, and/or undesirable paravalvular leakage and/or regurgitation at the implantation site. More particularly, for example, a prosthesis that is positioned too deep relative to the native annulus or placed unevenly within the native annulus in terms of depth may cause conduction disturbances and the incidence of permanent pacemaker increases (PPM) post-implantation may increase. If a prosthesis is positioned too shallow relative to the native annulus, there is a risk of valve embolization and patient death. Thus, it is imperative that the prosthesis be accurately located relative to the native annulus prior to full deployment of the prosthesis.

Embodiments hereof relate to an improved expandable transcatheter valve prosthesis configured to address one or more of the afore-mentioned complications.

BRIEF SUMMARY OF THE INVENTION

Embodiments hereof relate to a transcatheter valve prosthesis includes a stent having a crimped configuration for delivery within a vasculature and an expanded configuration for deployment within a native heart valve. The stent includes an inflow portion formed proximate to an inflow end of the stent, an outflow portion formed proximate to an outflow end of the stent, and a transition portion extending between the inflow portion and the outflow portion. The inflow portion includes a plurality of crowns and a plurality of struts with each crown being formed between a pair of opposing struts, and a plurality of side openings are defined by the plurality of crowns and the plurality of struts. The outflow portion includes a plurality of crowns and a plurality of struts with each crown being formed between a pair of opposing struts. Endmost outflow crowns are formed at the outflow end of the stent. The transition portion includes a plurality of axial frame members extending between the inflow portion and the outflow portion. Each axial frame member extends in an axial direction from a crown of the inflow portion to at least a crown of the outflow portion. Each axial frame member has a first end adjacent to the crown of the inflow portion, the first end having a reduced width relative to a width of a length of the axial frame member between the first end and the crown of the outflow portion. A prosthetic valve is disposed within and secured to at least the transition portion of the stent, the prosthetic valve being configured to block blood flow in one direction to regulate blood flow through a central lumen of the stent.

Embodiments hereof relate to a transcatheter valve prosthesis includes a stent having a crimped configuration for delivery within a vasculature and an expanded configuration for deployment within a native heart valve. The stent includes a plurality of axial frame members, an inflow portion, and an outflow portion. The inflow portion includes at least three rows of struts and crowns formed between adjacent pairs of the struts, and the at least three rows of the inflow portion are formed between an inflow end of the axial frame members and an inflow end of the stent. The outflow portion includes a single row of struts and crowns formed between adjacent pair of the struts. The outflow portion is coupled to an outflow end of the axial frame members, and exactly two struts of the plurality of struts of the outflow portion are disposed between adjacent axial frame members. Each axial frame member extends in an axial direction from a crown of the inflow portion to at least a crown of the outflow portion. Each axial frame member has a first end adjacent to a crown of the inflow portion, the first end having a reduced width relative to a width of a length of the axial frame member between the first end and the crown of the outflow portion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Figure 1:
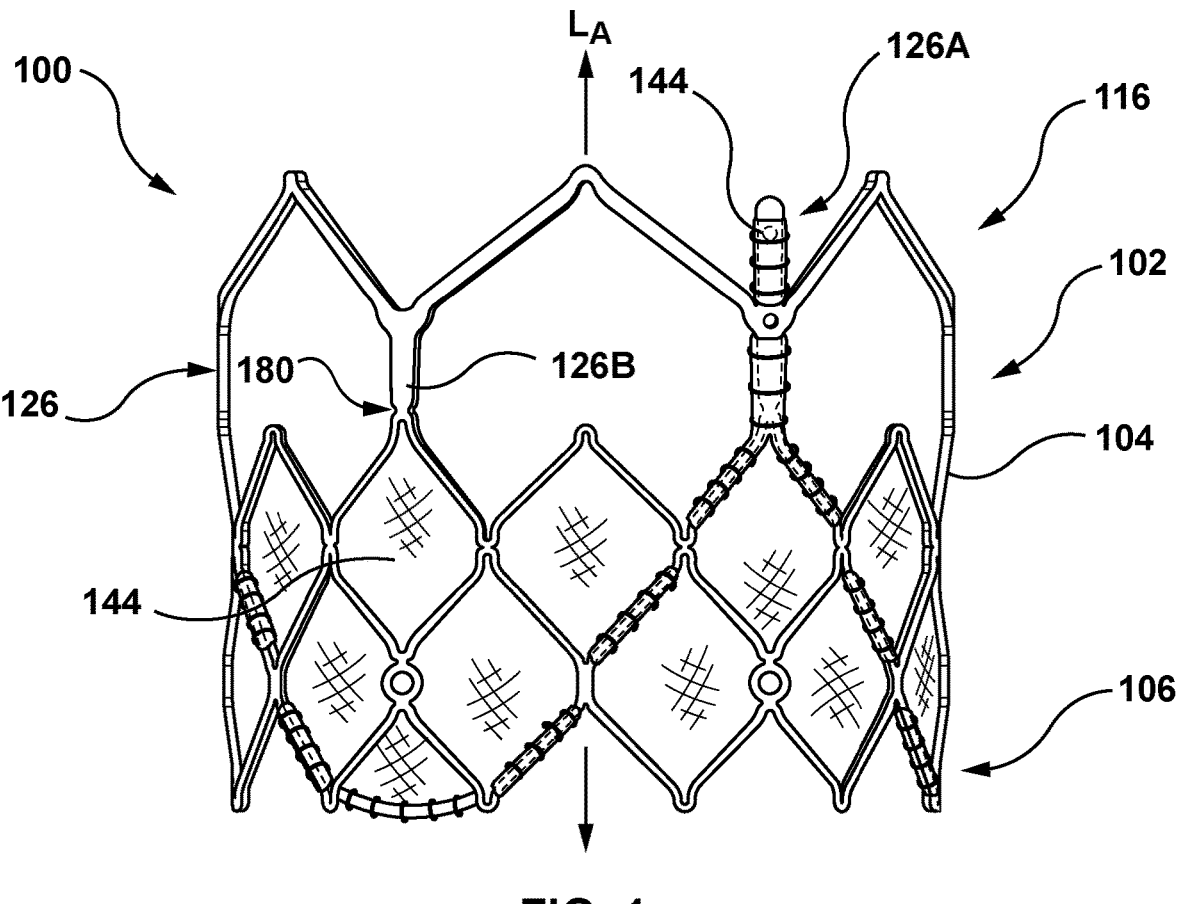
FIG. 1 is a side view of a transcatheter valve prosthesis according to an embodiment hereof, wherein the transcatheter valve prosthesis is in an expanded configuration.

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of an aortic heart valve, the invention may also be used where it is deemed useful in other valved intraluminal sites that are not in the heart. For example, the present invention may be applied to other heart valves or venous valves as well. Furthermore, there is no intention to be bound by any expressed or implied theory presented in the preceding technical field, background, brief summary or the following detailed description.

Embodiments hereof relate to a transcatheter valve prosthesis that includes a plurality of radiopaque markers at an inflow portion thereof. The transcatheter valve prosthesis is particularly configured to symmetrically collapse or crimp into a crimped or non-expanded configuration for delivery to ensure that the plurality of radiopaque markers forms a plane which is orthogonal to a longitudinal axis of the transcatheter valve prosthesis. Symmetry is particularly important in the crimped configuration because during implantation of a transcatheter valve prosthesis, the operator uses the radiopaque markers to adjust the depth of the transcatheter valve prosthesis in situ. As described herein, it is imperative that the transcatheter valve prosthesis be deployed in the accurate longitudinal or axial location relative to the native annulus. It is important that the transcatheter valve prosthesis crimps symmetrically rather than in a skewed or non-symmetrical form, because if the prosthesis is skewed or non-symmetrical when crimped, the radiopaque markers will appear longitudinally offset from another and generate confusion for the operator. If the radiopaque markers appear longitudinally offset from each other when crimped, it is unclear which marker (i.e., the higher or lower marker) should be used to gauge the depth of the transcatheter valve prosthesis in situ. In addition, if the prosthesis is skewed or non-symmetrical when crimped, the frame of the transcatheter valve prosthesis may damage valve leaflets and impact leaflet durability and/or performance. However, when the transcatheter valve prosthesis crimps symmetrically, the radiopaque markers at the inflow portion are longitudinally aligned and thus the radiopaque markers form clear and unambiguous landmarks used to gauge the depth of the transcatheter valve prosthesis in situ. Embodiments hereof relate to a transcatheter valve prosthesis having an integral symmetrical crimping feature integrated into the frame thereof that improves the crimp symmetry of the transcatheter valve prosthesis. Symmetrical crimping of the transcatheter valve prosthesis ensures that the plurality of radiopaque markers at the inflow end form a plane which is orthogonal to the longitudinal axis of the transcatheter valve prosthesis and therefore improves accuracy of the depth positioning of the transcatheter valve prosthesis in situ.

Figure 1A:
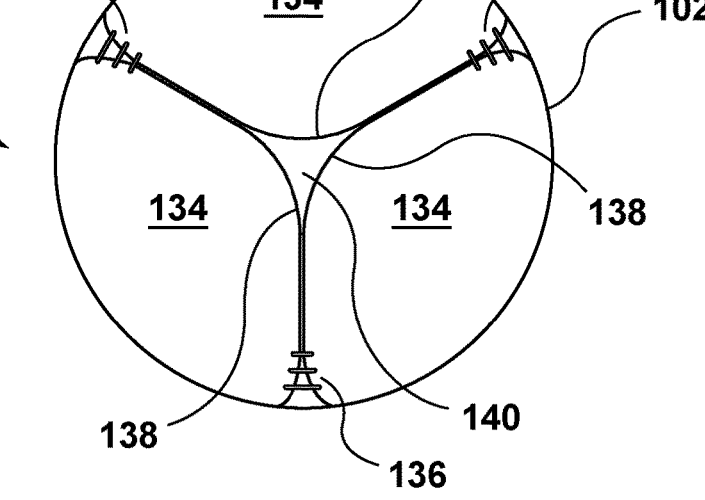
FIG. 1A is an end view illustration of the transcatheter valve prosthesis of FIG. 1.
Figure 2:
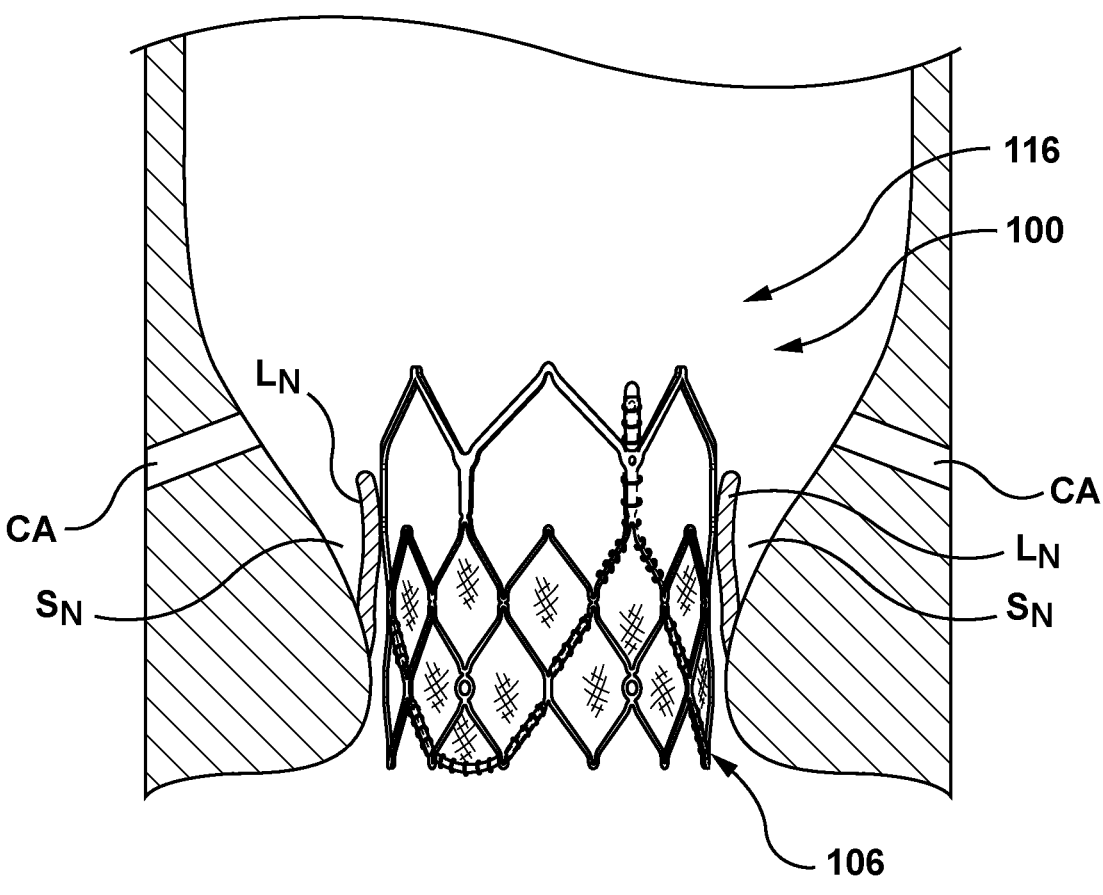
FIG. 2 is a side view illustration of the transcatheter valve prosthesis of FIG. 1 implanted within a native aortic valve annulus, wherein the transcatheter valve prosthesis is in the expanded configuration.

The transcatheter valve prosthesis according to embodiments hereof will be described in more detail with respect to the figures. More particularly, a transcatheter valve prosthesis 100 includes a radially-expandable frame or stent 102 and a prosthetic valve 132. The transcatheter valve prosthesis 100 has a longitudinal axis LA as shown in FIG. 1. The stent 102 is generally tubular, and is self, mechanically or balloon expandable, having a crimped configuration for delivery within a vasculature and an expanded configuration for deployment within a native heart valve. FIG. 1 is a side view of the transcatheter valve prosthesis 100 in the expanded configuration, while FIG. 1A is an end view illustration of the transcatheter valve prosthesis 100. When the transcatheter valve prosthesis 100 is deployed within the valve annulus of a native heart valve, the stent 102 of the transcatheter valve prosthesis 100 is configured to be radially expanded within native valve leaflets of the patient's defective valve, to thereby retain the native valve leaflets in a permanently open state as shown in FIG. 2. In embodiments hereof, the transcatheter valve prosthesis 100 is configured for replacement for an aortic valve such that an inflow end 106 of the transcatheter valve prosthesis 100 extends into and anchors within the aortic annulus of a patient's left ventricle, while an outflow end 116 of the transcatheter valve prosthesis 100 is positioned within the aortic sinuses.

The stent 102 of the transcatheter valve prosthesis 100 may be a unitary frame or scaffold that supports the prosthetic valve 132 including one or more valve leaflets 134 within the interior of the stent 102. The prosthetic valve 132 is capable of blocking flow in one direction to regulate flow there-through via the valve leaflets 134 that may form a bicuspid or tricuspid replacement valve. FIG. 1A is an end view of FIG. 1 taken from the outflow end 116 of the prosthesis and illustrates an exemplary tricuspid valve having three valve leaflets 134, although a bicuspid leaflet configuration may alternatively be used in embodiments hereof. More particularly, as the transcatheter valve prosthesis 100 is configured for placement within a native aortic valve which typically has three leaflets, the prosthetic valve 132 may include three valve leaflets 134. However, the transcatheter valve prosthesis 100 is not required to have the same number of leaflets as the native valve. If the transcatheter valve prosthesis 100 is alternatively configured for placement within a native valve having two leaflets such as the mitral valve, the prosthetic valve 132 may include two or three valve leaflets, or a different number of leaflets. The valve leaflets 134 may be attached to a graft material 144 which encloses or lines a portion of the stent 102 as would be known to one of ordinary skill in the art of prosthetic tissue valve construction. The valve leaflets 134 are sutured or otherwise securely and sealingly attached along their bases to the interior surface of the graft material 144, or otherwise attached to the stent 102. Adjoining pairs of leaflets are attached to one another at their lateral ends to form commissures 136, with free edges 138 of the valve leaflets 134 forming coaptation edges that meet in area of coaptation 140.

The valve leaflets 134 may be made of pericardial material; however, the valve leaflets 134 may instead be made of another material. Natural tissue for the valve leaflets 134 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as the valve leaflets 134 include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 144 may enclose or line the stent 102 as would be known to one of ordinary skill in the art of prosthetic tissue valve construction. Graft material 144 may be a natural or biological material such as pericardium or another membranous tissue such as intestinal submucosa. Alternatively, graft material 144 may be a low-porosity woven fabric, such as polyester, Dacron fabric, or PTFE, which creates a one-way fluid passage when attached to the stent. In one embodiment, graft material 144 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

As previously stated, the stent 102 can be balloon-expandable as would be understood by one of ordinary skill in the art. As such, the stent 102 is made from a plastically deformable material such that when expanded by a dilatation balloon, the stent 102 maintains its radially expanded configuration. The stent 102 may be formed from stainless steel or other suitable metal, such as platinum iridium, cobalt chromium alloys such as MP35N, or various types of polymers or other materials known to those skilled in the art, including the materials described above coated with various surface deposits to improve clinical functionality. The stent 102 is configured to be rigid such that it does not deflect or move when subjected to in-vivo forces, or such that deflection or movement is minimized when subjected to in-vivo forces. In an embodiment, the radial stiffness (i.e., a measurement of how much the stent 102 deflects when subjected to in-vivo forces) of the stent 102 is between 80 N/m and 120 N/m, and the radial stiffness of the stent 102 scaled across the deployed height thereof is approximately 5 N/mm$^2$. In an embodiment, the radial stiffness of the stent 102 is greater than 100 N/m. Further, in an embodiment, the device recoil (i.e., a measurement of how much the stent 102 relaxes after balloon deployment) is below 15% and the approximately recoil after deployment is between 0.5 mm and 2 mm. Further, in an embodiment, the device crush or yield (i.e., the radial force at which the stent 102 yields) is approximately 200 N.

Delivery of the transcatheter valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. The transcatheter valve prosthesis 100 has a crossing profile of between 15-30 Fr, the crossing profile being defined as the outside diameter (OD) of the transcatheter valve prosthesis 100 after it is crimped onto the balloon and allowed to recoil from the crimping action. During delivery, the transcatheter valve prosthesis 100 remains compressed until it reaches a target diseased native heart valve, at which time a balloon of a delivery system is inflated in order to radially expand the transcatheter valve prosthesis 100 in situ. The delivery system is then removed and the transcatheter valve prosthesis 100 remains deployed within the native target heart valve.

FIG. 2 illustrates the transcatheter valve prosthesis 100 implanted in situ within a native aortic valve annulus, which is shown in section, having native leaflets $L_N$ and corresponding native sinuses $S_N$. FIG. 2 also illustrates placement of the coronary arteries CA. The transcatheter valve prosthesis 100 is configured for intra-annular placement within a native aortic valve. More particularly, the inflow end 106 of the transcatheter valve prosthesis 100 extends into and anchors within the aortic annulus of a patient's left ventricle, while the outflow end 116 of the transcatheter valve prosthesis 100 is positioned within the aortic sinuses, with no portion of the transcatheter valve prosthesis 100 extending into the patient's ascending aorta. When the transcatheter valve prosthesis 100 is deployed within the valve annulus of a native heart valve, the stent 102 is configured to be expanded within native valve leaflets $L_N$ of the patient's defective valve, to thereby retain the native valve leaflets in a permanently open state. A height or length of the stent 102 in the expanded configuration is between 12 and 24 mm, the height being measured from the most proximal part thereof (endmost inflow crowns 110A, which will be described in more detail herein) to the most distal part thereof (endmost outflow crowns 120A, which will be described in more detail herein). In an embodiment hereof, a height or length of the stent 102 in the expanded configuration is between 15 and 24 mm. For example, in an embodiment the stent 102 has diameter of between 21-24 mm and a height of 17 mm. In another embodiment, the stent 102 has diameter of between 24-27 mm and a height of 19 mm. In yet another embodiment, the stent 102 has diameter of between 27-30 mm and a height of 21 mm. In another embodiment hereof, the stent 102 may be configured for supra-annular placement.

Figure 3:
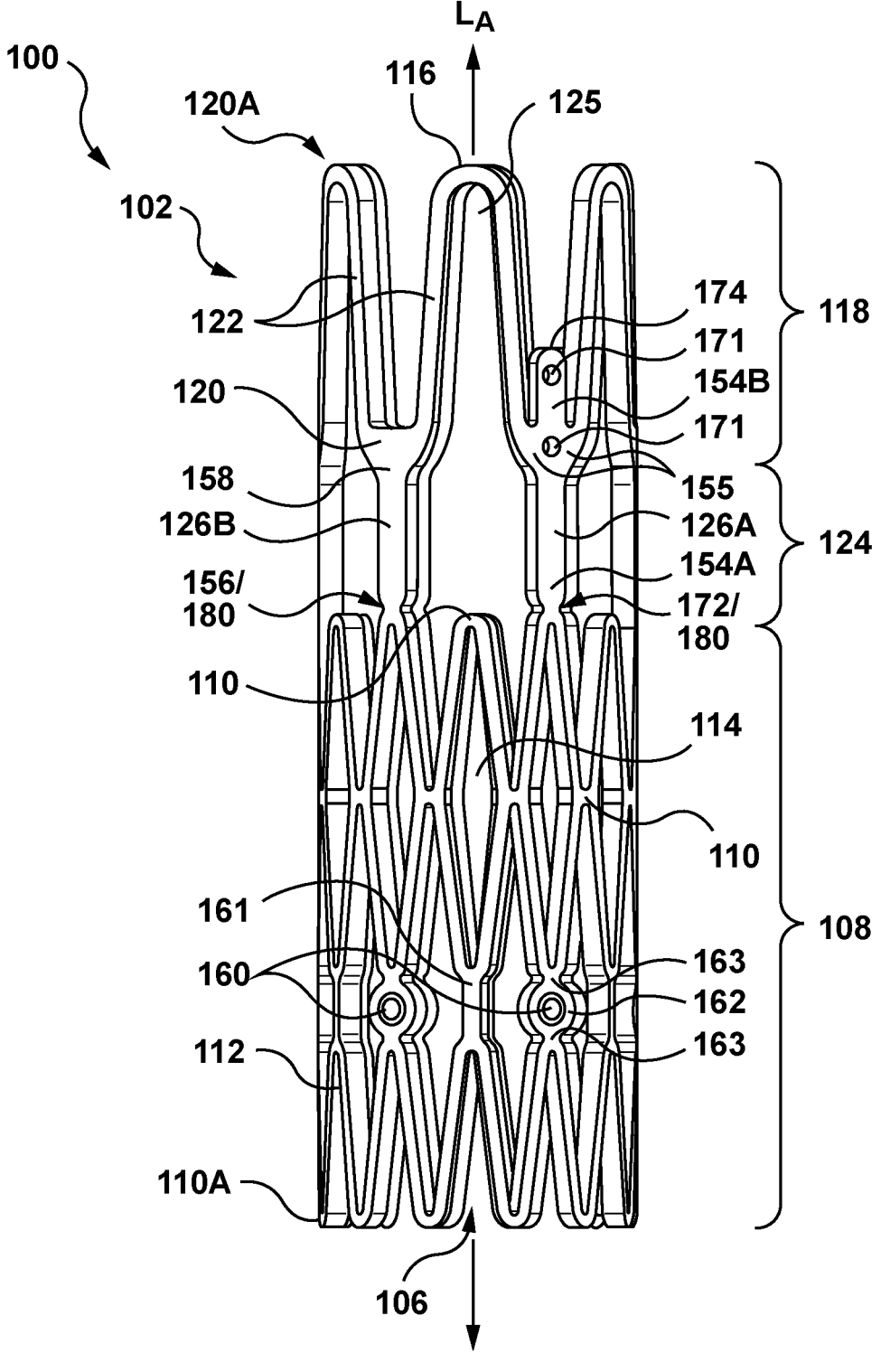
FIG. 3 is a perspective view of the stent of the transcatheter valve prosthesis of FIG. 1, wherein the stent is in a non-expanded or crimped configuration.
Figure 4:
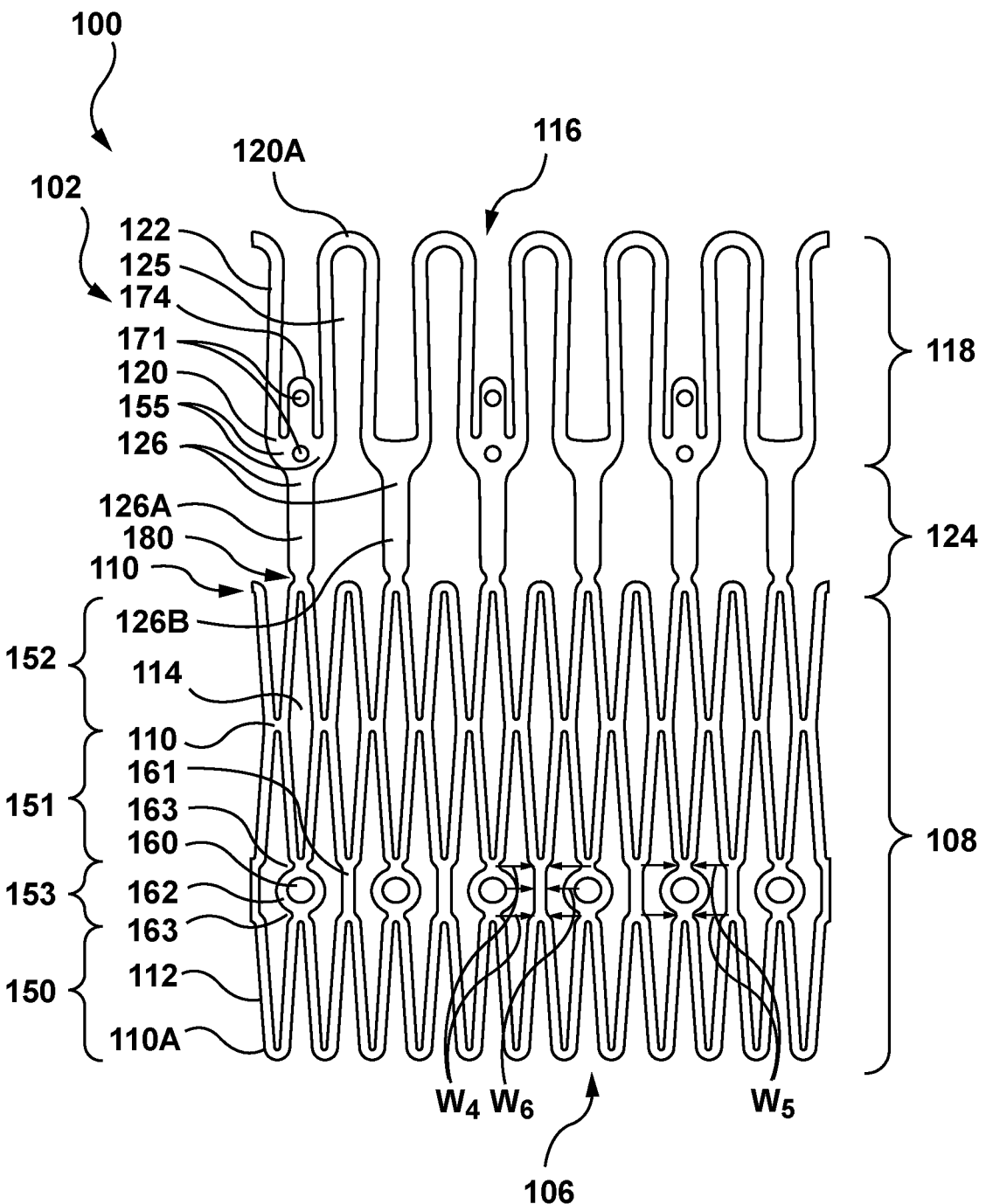
FIG. 4 is a side view of the stent of the transcatheter valve prosthesis of FIG. 1, wherein the stent is in the non-expanded or crimped configuration and has been laid flat for illustrative purposes only.
Figure 5:
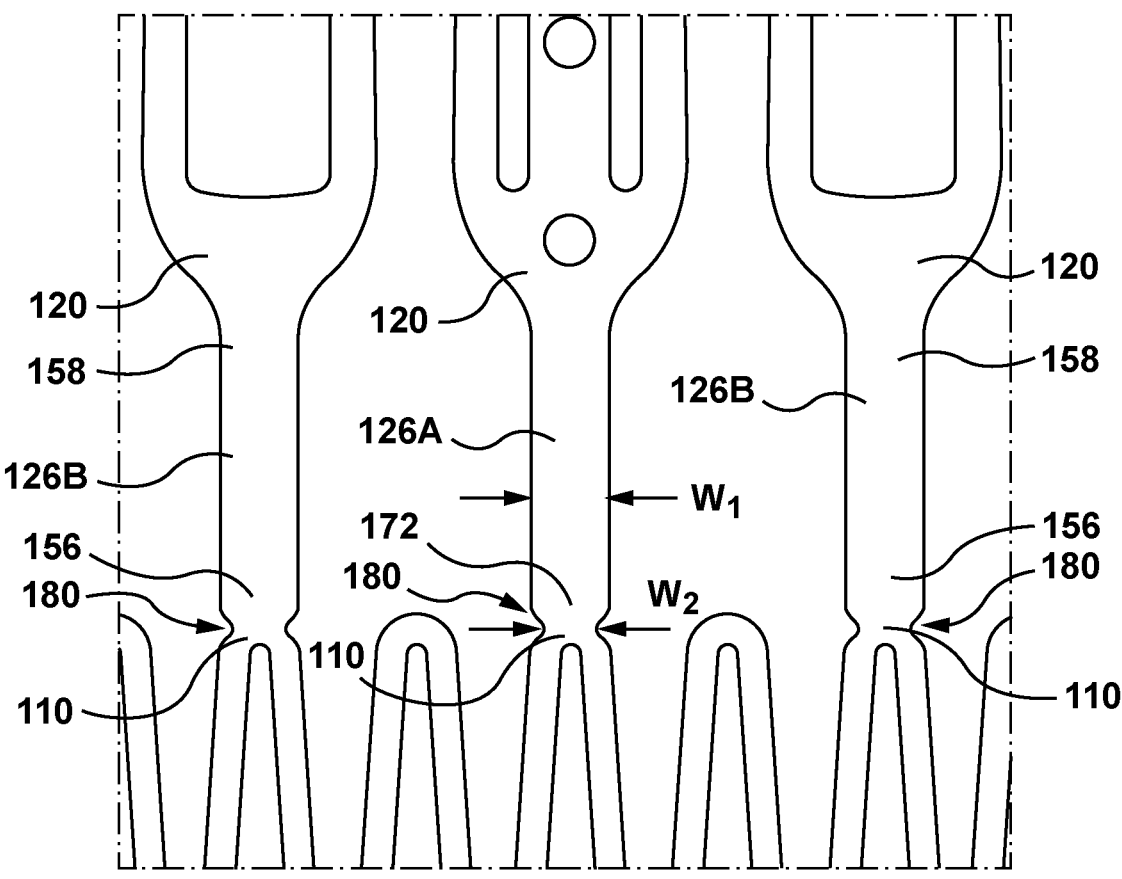
FIG. 5 is an enlarged view of a portion of FIG. 4.
Figure 6:
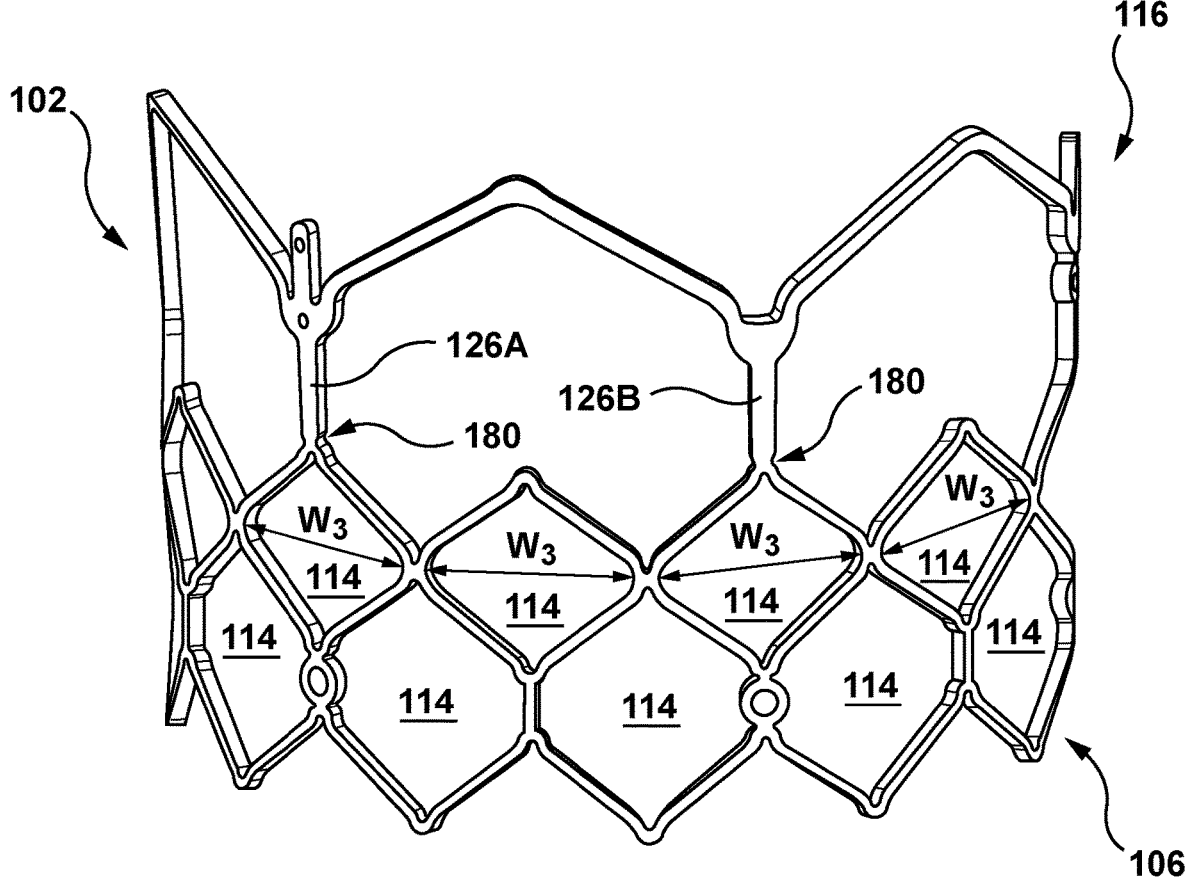
FIG. 6 is a perspective view of the stent of the transcatheter valve prosthesis of FIG. 1, wherein the stent is in the expanded configuration.
Figure 7:
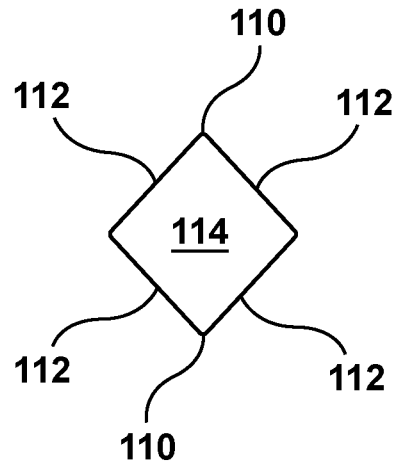
FIG. 7 is an enlarged side view of a single cell or side opening of an inflow portion of the stent of the transcatheter valve prosthesis of FIG. 1, wherein the stent is in the expanded configuration.
Figure 8:
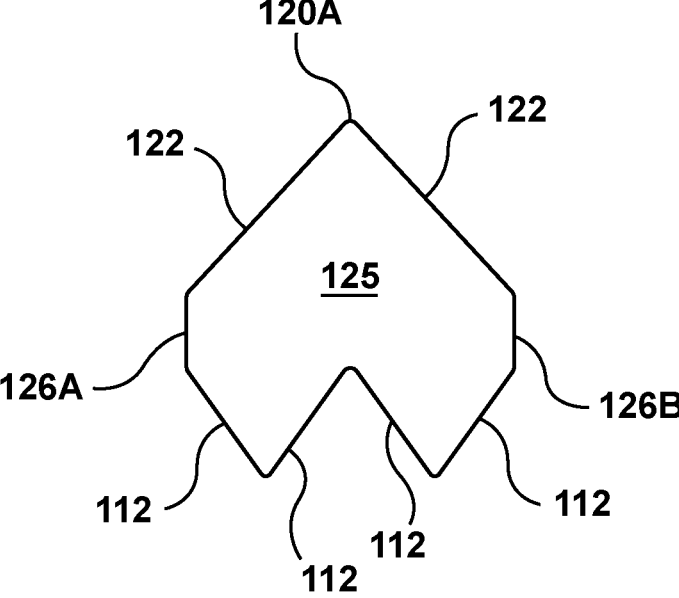
FIG. 8 is an enlarged side view of a single endmost opening of the stent of the transcatheter valve prosthesis of FIG. 1, wherein the stent is in the expanded configuration.
Figure 9:
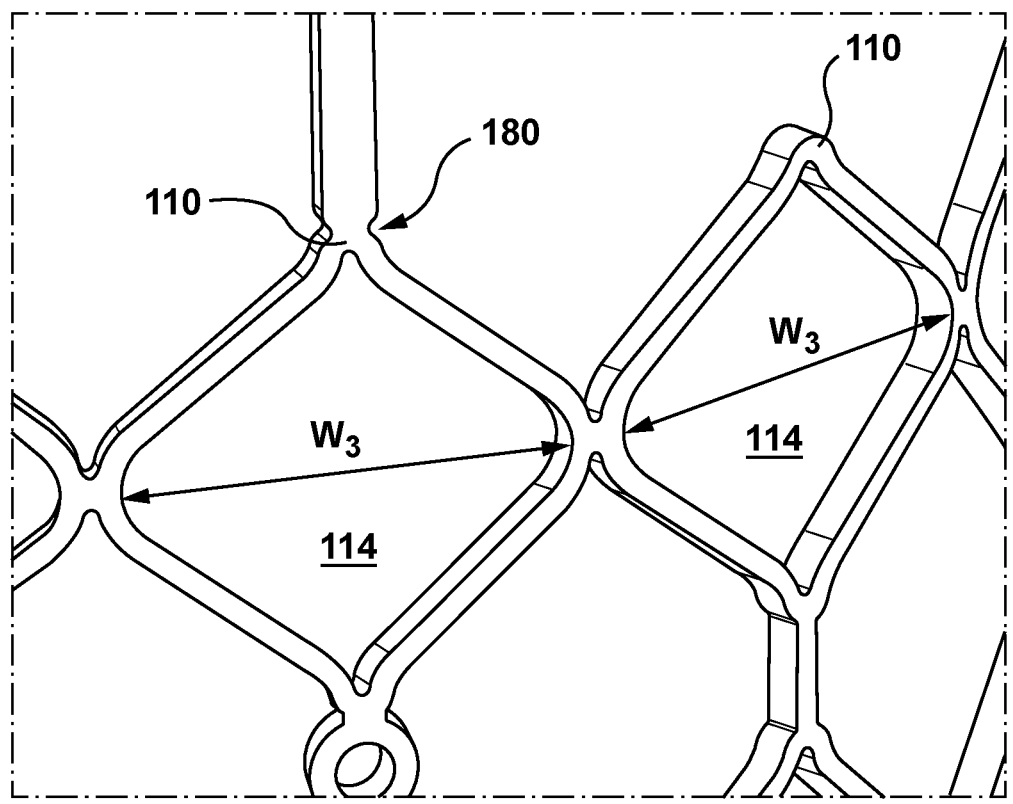
FIG. 9 is an enlarged view of a portion of FIG. 6.
Figure 10:
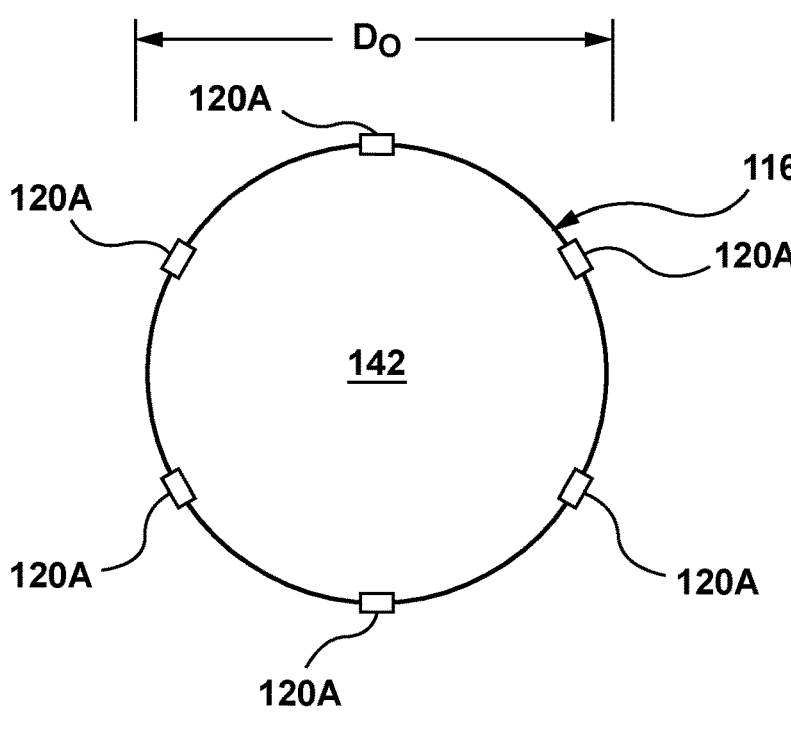
FIG. 10 is an end view of an outflow end of the stent of the transcatheter valve prosthesis of FIG. 1.
Figure 11:
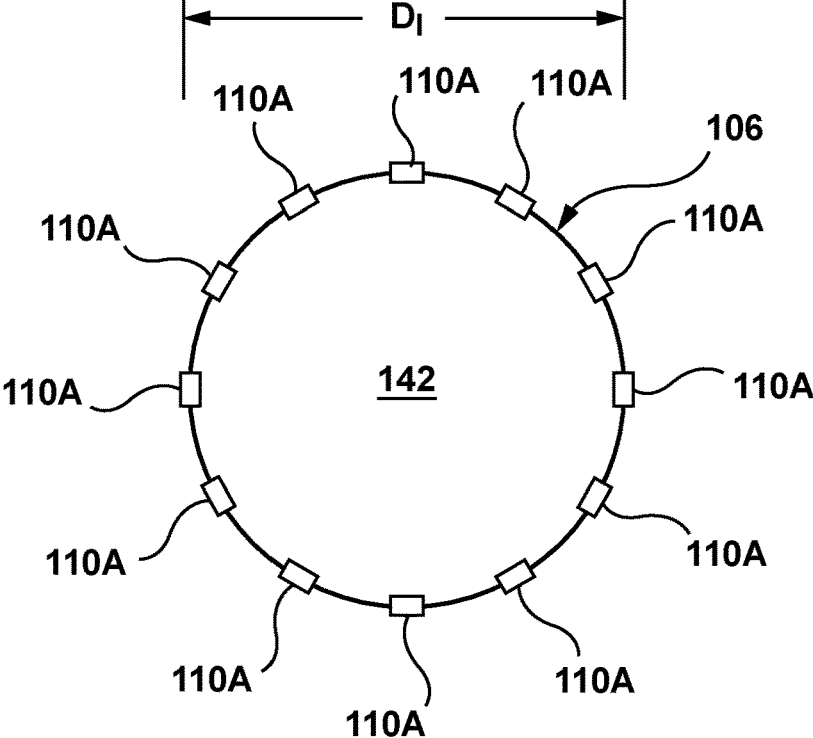
FIG. 11 is an end view of an inflow end of the stent of the transcatheter valve prosthesis of FIG. 1.

The stent 102 will now be described in more detail with respect to FIGS. 3-11. The stent 102 has a non-expanded or crimped configuration, which is shown in FIGS. 3-5, and an expanded configuration, which is shown in FIGS. 6-11. Non-expanded or crimped configuration as used herein refers to the configuration of the stent 102 or the transcatheter valve prosthesis 100 after crimping onto a balloon of a balloon catheter for delivery. Expanded configuration as used herein refers to the configuration of the stent 102 or the transcatheter valve prosthesis 100 after radial expansion by the balloon. FIG. 3 is a perspective view of the stent 102 in the non-expanded or crimped configuration, while FIG. 4 shows the stent 102 in the non-expanded or crimped configuration that has been laid flat for illustrative purposes only. FIG. 5 is an enlarged view of a portion of FIG. 4. FIG. 6 is a perspective view of the stent 102 in the expanded configuration, while FIGS. 7, 8, and 9 are enlarged portions of FIG. 6. FIG. 10 is an end view of the outflow end 116 of the stent 102 when the stent is in the expanded configuration, while FIG. 11 is an end view of the inflow end 106 of the stent 102 when the stent is in the expanded configuration.

The stent 102 includes an inflow portion 108, an outflow portion 118, and a transition portion 124 bridging, connecting, or otherwise extending between the inflow portion 108 and the outflow portion 118. While the stent 102 is described as including the transition portion 124, one skilled in the art will realize that the transition portion 124 may form a portion of the inflow portion 108 and/or the outflow portion 118. The stent 102 is a tubular component defining a central lumen or passageway 142, and further defines the inflow or proximal end 106 and the outflow or distal end 116 of the transcatheter valve prosthesis 100. As best shown in FIGS. 10 and 11, when expanded, a diameter $D_I$ of the inflow end 106 of the stent 102 is substantially the same as a diameter $D_O$ of the outflow end 116 of the stent 102. In an embodiment, the diameters $D_I$ and $D_O$ may range between 18 and 30 mm in order to accommodate dimensions of the native valve anatomy. Stated another way, it may be desirable for the transcatheter valve prosthesis 100 to be available in varying size increments to accommodate varying diameters or sizes of a patient's native annulus. The stent 102 may be formed by a laser-cut manufacturing method and/or another conventional stent forming method as would be understood by one of ordinary skill in the art. The cross-section of the stent 102 may be circular, ellipsoidal, rectangular, hexagonal, square, trapezoidal, or other polygonal shape, although at present it is believed that circular, ellipsoidal, or trapezoidal may be preferable with the transcatheter valve prosthesis 100 being provided for replacement of an aortic valve. Similarly, the cross-section of the various struts that form the stent 102 may be circular, ellipsoidal, rectangular, hexagonal, square, trapezoidal, wedge-shaped, or other polygonal shape.

The inflow portion 108 is formed proximate to the inflow end 106 of the stent. The inflow portion 108 includes a plurality of crowns 110 and a plurality of struts 112 with each crown 110 being formed between a pair of opposing struts 112. Each crown 110 is a curved segment or bend extending between opposing struts 112. The inflow portion 108 is tubular, with a plurality of side openings 114 being defined by the plurality of crowns 110 and the plurality of struts 112. In an embodiment, the plurality of side openings 114 may be diamond-shaped. More particularly, as best shown in FIG. 7 which is a side view of a single side opening 114 of the inflow portion 108 of the stent 102, each side opening 114 is formed by two pairs of opposing crowns 110 and four struts 112 therebetween. Each side opening 114 is symmetrical for easier integration with the prosthetic valve 132. A series of endmost inflow side openings 114A and a series of endmost inflow crowns 110A are formed at the inflow end 106 of the stent 102. The inflow end 106 of the stent 102 has a total of twelve endmost inflow crowns 110A, as best shown in the end view of FIG. 11.

Figure 3A:
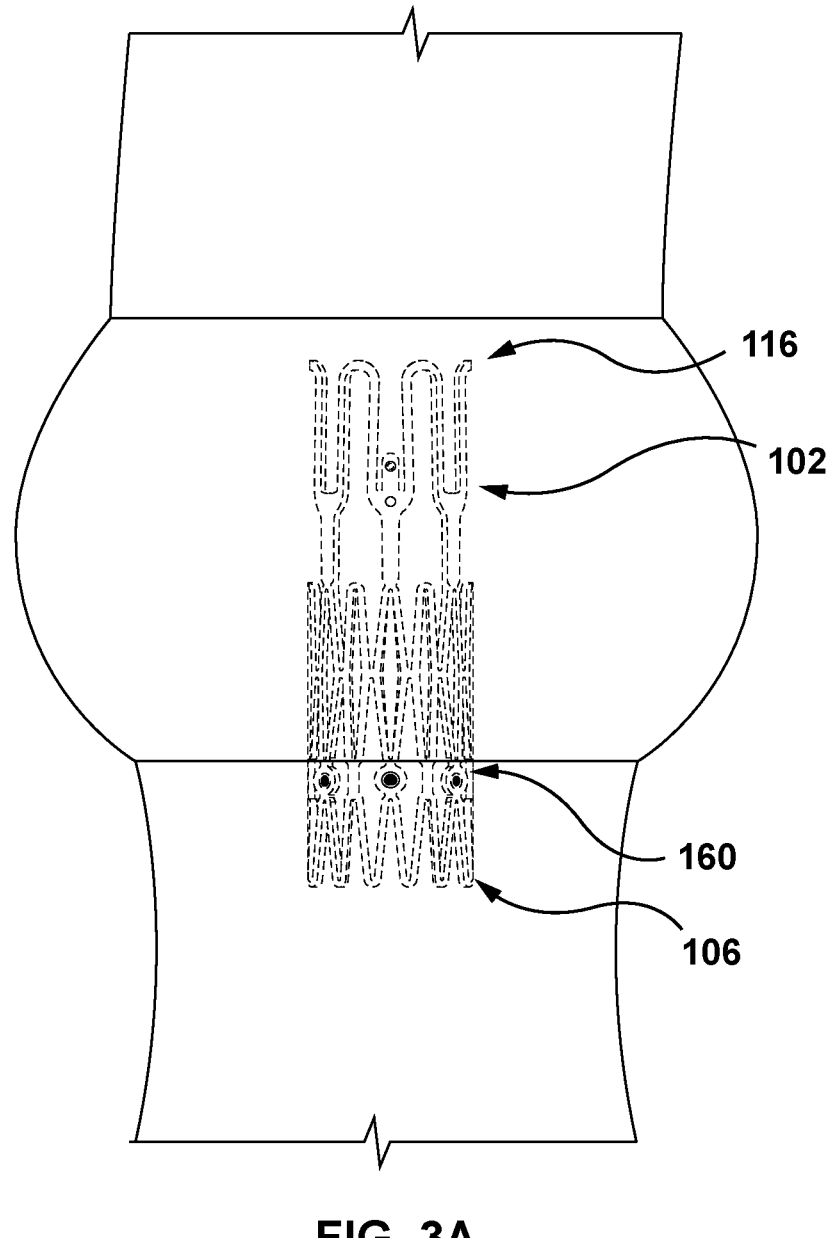
FIG. 3A is a side view illustration representing an image under fluoroscopy of the stent of FIG. 3 within a native aortic valve annulus, wherein the stent is in the non-expanded or crimped configuration.

The inflow portion 108 of the stent 102 also includes a plurality of inflow markers 160 that can be utilized in orientation of the transcatheter valve prosthesis 100, in situ to ensure the proper placement in the native anatomy of a subject. As previously described, the transcatheter valve prosthesis 100 needs to be properly aligned in the axial or longitudinal direction so that the transcatheter valve prosthesis 100 properly engages the native leaflets/tissue of the target site, e.g., the aortic annulus, without causing conduction blockages by implanting too deep or causing an embolization of the transcatheter valve prosthesis 100 because it was implanted too high. During implantation of the transcatheter valve prosthesis 100, the operator uses the plurality of inflow markers 160 to adjust the depth of the transcatheter valve prosthesis 100 in situ because it is imperative that the transcatheter valve prosthesis 100 be deployed in the accurate longitudinal or axial location relative to the native annulus. When the transcatheter valve prosthesis 100 is compressed into the non-expanded or crimped configuration for delivery, it is important that the transcatheter valve prosthesis 100 crimps symmetrically so that the plurality of inflow markers 160 are longitudinally aligned and visible in an array that forms a plane which is orthogonal to the longitudinal axis LA of the transcatheter valve prosthesis 100 as shown in FIG. 3A. With the plurality of inflow markers 160 longitudinally aligned, the plurality of inflow markers 160 form clear and unambiguous landmarks used to gauge the depth of the transcatheter valve prosthesis 100 in situ. FIG. 3A is a side view illustration representing an image under fluoroscopy of the stent 102 within a native aortic valve annulus, the stent 102 being in the non-expanded or crimped configuration and the plurality of inflow markers 160 are longitudinally aligned and visible in an array that forms a plane which is orthogonal to the longitudinal axis LA of the transcatheter valve prosthesis 100. During delivery, an operator aligns the plurality of inflow markers 160 with the basal plane of the native anatomy as shown in FIG. 3A. Thus, the plurality of inflow markers 160 allows for better depth positioning of the transcatheter valve prosthesis 100 such that it can be more accurately deployed and reduce the incidence rate of permanent pacemaker (PPM) post-implantation. To align the transcatheter valve prosthesis 100, a delivery system (not shown) can be manipulated (e.g., advanced, retracted, etc.) until the plurality of inflow markers 160 align with the basal plane of the native anatomy. As such, the transcatheter valve prosthesis 100 can be positioned at a proper depth within the target site, thereby ensuring proper engagement with the native tissue.

The inflow markers 160 are positioned towards the inflow end 106 of the stent 102 in the inflow portion 108. The inflow markers 160 form a ring of distinct marker points around the circumference of the stent 102, wherein each distinct marker point is equal distance from the inflow end 106. The inflow markers 160 are preferably located at the lengthwise location of the stent 102 that is desired to be aligned with the annulus of the native heart valve when the transcatheter valve prosthesis 100 is deployed at the native heart valve. More particularly, as illustrated in FIG. 4, the stent 102 can include three rows of the struts 112: a first row 150 of the struts 112 formed proximate to the inflow end 106, a second row 151 of the struts 112 formed between the first row 151 and a third row 152, and the third row 152 of struts 112 formed proximate to the transition portion 124. In an embodiment, the inflow markers 160 can be positioned at the intersection 153 of the first row 150 and the second row 151. For example, in embodiments hereof, the inflow markers 160 are positioned at every other intersection of a pair of the struts 112 of the first row 150 and a pair of the struts 112 of the second row 151. The inflow markers 160 are circumferentially aligned with each other around a circumference of the stent 102. One skilled in the art will realize that other positioning of the inflow markers 160 may be utilized. For example, the inflow markers 160 can be positioned on the struts 112 and/or can be positioned at different distances from the inflow end 106.

The inflow markers 160 include radiopaque or other material that allow the inflow markers 160 to be detected and/or viewed under fluoroscopy during the implantation of the transcatheter valve prosthesis 100. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc. In embodiments, the inflow markers 160 can be formed in any shape to assist in the alignment of the transcatheter valve prosthesis 100. In embodiments hereof, the inflow markers 160 are formed having a circular cross-sectional shape. In other embodiments, the inflow markers 160 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the inflow markers 160 may be provided to provide a benefit for a given application. In an embodiment, each inflow marker 160 is attached to the stent 102 within a containment member 162. The containment member 162 is configured as a hollow structure or opening in the stent 102 which can receive or hold an inflow marker 160.

When a marker 160 is not present, an axial extension 161 is disposed at the intersection 153, between a pair of the struts 112 of the first row 150 and a pair of the struts 112 of the second row 151. Thus, the inflow portion 108 includes a plurality of containment members 162 and a plurality of axial extensions 161, with an axial extension 161 disposed between a pair of adjacent containment members 162. The axial extensions 161 extend substantially parallel to the longitudinal axis LA of the stent 102. Each axial extension

161 extends between a first crown 110 of the inflow portion 108 and a second crown 110 of the inflow portion 108, with a first transition area extending between a first end of the axial extension 161 and the first crown 110 and a second transition area extending between a second end of the axial extension 161 and the second crown 110. At the areas of transition between the first and second crowns 110 of the inflow portion 108 and the axial extension 161, each area of transition has a width $W_4$ as shown in FIG. 4. Each axial extension 161 has a constant or uniform width $W_6$ along a length thereof, or stated another way, has a constant or uniform width $W_6$ from the first end to the second end thereof. In an embodiment, width $W_6$ of each axial extension 161 is less than the width $W_4$. In an embodiment, width $W_6$ is between 60% and 90% of the width $W_4$.

At the top and bottom of each containment member 162, a junction 163 extends between a crown 110 of the inflow portion 108 and the containment member 162. Stated another way, each junction 163 is a transition area between a crown 110 of the inflow portion 108 and a containment member 162. Each junction 163 has a width $W_5$ as shown in FIG. 4. In an embodiment, width $W_4$ is substantially equal to width $W_5$. In another embodiment, width $W_4$ is slightly relatively less than width $W_5$, with width $W_4$ being between 75% and 99% of the width $W_5$. By providing width $W_4$ to be substantially equal to width $W_5$, or only slightly relatively less than $W_5$, the geometry of the crowns 110 at each of these areas have a more similar geometry, thereby improving crimp and expansion symmetry of the transcatheter valve prosthesis 100. These relative dimensions of $W_4$ and $W_5$ result in uniform effective strut dimensions in the inflow portion 108 of the stent 102 and further provides a desirable compression and expansion response.

While the transcatheter valve prosthesis 100 is described herein as including the plurality of inflow markers 160, one skilled in the art will realize that the transcatheter valve prosthesis 100 may include additional markers, such as, for example, one or more outflow markers to assist with the alignment of the commissure posts 126A as described in U.S. Prov. App. No. 62/985,124, filed on Mar. 4, 2020 and assigned to the same assignee as the present application, which is herein incorporated by reference in its entirety. Outflow markers, in conjunction with the inflow markers 160, can be utilized to align circumferential or rotational orientation of the transcatheter valve prosthesis 100 to avoid blocking the ostia of the coronary arteries.

The outflow portion 118 is formed proximate to the outflow end 116 of the stent. The outflow portion 118 includes a plurality of crowns 120 and a plurality of struts 122 with each crown 120 being formed between a pair of opposing struts 122. Each crown 120 is a curved segment or bend extending between opposing struts 122. The outflow portion 118 can be configured in a shape that forms a central lumen or passageway, for example, a ring. A series of endmost outflow crowns 120A are formed at the outflow end 116 of the stent 102. The outflow end 116 of the stent 102 has a total of six endmost outflow crowns 120A, as best shown in the end view of FIG. 10. In an embodiment hereof, the total of the endmost inflow crowns 110A are twice a total of the endmost outflow crowns 120A. In this embodiment, the endmost outflow crowns 120A are not connected to axial frame members 126 of the transition portion 124 but rather may be considered to be free or unattached while the remaining outflow crowns 120 of the outflow portion 118 are connected to the axial frame members 126 and disposed closer to the inflow end 106 than the endmost outflow crowns 120A.

The transition portion 124 bridges, connects, or otherwise extends between the inflow portion 108 and the outflow portion 118. The prosthetic valve 132 is disposed within and secured to at least the transition portion 124 of the stent 102 at the commissure posts thereof. In addition, the prosthetic valve 132 may also be disposed within and secured to the inflow portion 108 of the stent 102. As will be described in more detail herein, the transition portion 124 is particularly configured to improve crimp symmetry of the transcatheter valve prosthesis 100. Symmetry in the crimped or non-expanded configuration ensures that the plurality of inflow markers 160 of the stent 102 form a plane which is orthogonal to the longitudinal axis LA of the transcatheter valve prosthesis 100 which may be used during longitudinal or axial positioning of the transcatheter valve prosthesis 100 in situ as described above.

The transition portion 124 includes up to six axial frame members 126, with three of the axial frame members 126 being commissure posts 126A and three of the axial frame members 126 being axial struts 126B. Each axial frame member 126 extends in an axial direction from a crown 110 of the inflow portion 108 to at least a crown 120 of the outflow portion 118. The axial frame members 126 are substantially parallel to the longitudinal axis LA of the stent 102. It will be understood by one of ordinary skill in the art that the longitudinal axis LA of the stent 102 is the same axis as the longitudinal axis LA of the transcatheter valve prosthesis 100. Each axial frame member 126 is disposed approximately halfway between a pair of adjacent endmost outflow crowns 120A. The axial frame members 126 aid in valve alignment and coaptation. More particularly, the axial frame members 126 reinforce or strengthen the commissure region of the prosthetic valve 132 by shaping the leaflets 134 and supporting the leaflets 134 during opening and closing thereof, and thus provide more reliable leaflet coaptation. Symmetrical cell expansion ensures that stent 102 crimps well onto a balloon of a balloon catheter for delivery. Poor crimp quality may lead to portions of the stent overlapping when crimped, which in turn may cause tissue damage to the valve leaflets of the prosthetic valve during the crimping process.

The commissure posts 126A are circumferentially spaced apart and aligned with and attached to a respective commissure of the three leaflets 134 of the prosthetic valve 132, and the axial struts 126B are disposed between adjacent commissure posts 126A. The commissure posts 126A may include holes or openings 171 formed therein configured to attach a respective commissure of the three leaflets 134 of the prosthetic valve 132 to the stent 102. The commissure posts 126A are covered with the graft material 144 as shown in FIG. 1 so as to be atraumatic, although such graft material is not required. In an embodiment, the commissure posts 126A are formed to have an axial length greater than the axial struts 126B. Each commissure posts 126A extends into the outflow portion 118 of the stent 102 to allow for commissure posts without increasing the overall height of the transcatheter valve prosthesis 100. More particularly, each axial strut 126B is an axial segment having a first end 156 connected to a crown 110 of the inflow portion 108 and a second end 158 connected to a crown 120 of the outflow portion 118. Stated another way, a crown 120 of the outflow portion 118 may be considered the outflow end of each axial strut 126B and a crown 110 of the inflow portion 108 may be considered the inflow end of each axial strut 126B. Conversely, each commissure post 126A is a relatively stiff, axial segment or planar bar having a first end 172 connected to a crown 110 of the inflow portion 108 while a second, unattached or free end 174 of each of the commissure posts 126A is disposed within the outflow portion 118. Stated another way, a crown 110 of the inflow portion 108 may be considered the inflow end of each commissure post 126A such that each commissure post 126A extends from struts 112 of the inflow portion 108 to the outflow end thereof, which is the unattached or free end 174 thereof. Because the commissure posts 126A are longer than the axial struts 126B, struts 122 of the outflow portion 118 intersect the commissure posts 126A at a central or mid-portion 155 thereof. The location of the connection between struts 122 of the outflow portion 118 to the mid-portions 155 of the commissure posts 126A is spaced a distance, in the direction of the inflow end 106, from the unattached or free end 174 of the commissure posts 126A and is also spaced a distance from the inflow end of the commissure posts 126A. As such, a first or transition portion 154A of each commissure post 126A is disposed in the transition portion 124 of the stent 102 between the mid-portion 155 and a crown 110 of the inflow portion 108 while an second or outflow portion 154B of each commissure post 126A is disposed in the outflow portion 118 of the stent 102 between the mid-portion 155 and the unattached or free end 174.

The outflow portions 154B of the commissure posts 126A function as support features that allow for the commissure posts 126A to further reinforce or strengthen the commissure region of the transcatheter valve prosthesis 100. Each outflow portion 154B extends into the outflow portion 118 of the stent 102 to allow for commissure posts 126A without increasing the overall height of the transcatheter valve prosthesis 100. The commissure posts 126A and benefits thereof are further described in U.S. Prov. App. No. 62/985,131, filed Mar. 4, 2020 and assigned to the same assignee as the present application, herein incorporated by reference in its entirety. Additionally, as described in U.S. Prov. App. No. 62/985,124, previously incorporated by reference in its entirety, the commissure posts 126A may include one or more additional holes or openings to support additional radiopaque markers for alignment.

The area of transition between a crown of the inflow portion 108 and each axial frame member 126 includes an integral symmetrical crimping feature that improves symmetry of the transcatheter valve prosthesis 100. More particularly, at the area of transition between a crown of the inflow portion 108 and each axial frame member 126, each axial frame member 126 includes a pair of cutouts 180 disposed on opposing sides of the first ends 156, 172 thereof to improve crimp and expansion symmetry of the transcatheter valve prosthesis 100. The cutouts 180 are removed or cut away material from the axial frame members 126 at the area of transition between a crown of the inflow portion 108 and each axial frame member 126. Due to the cutouts 180, during crimp of the stent 102, the struts forming the side openings 114 collapse or compress uniformly and elongate at the same rate circumferentially, resulting in a more symmetrical crimped configuration. During expansion, the struts forming the side openings 114 foreshorten at the same rate circumferentially resulting in a more uniform width of the side openings 114 in the expanded configuration. Although the cutouts 180 are described herein as removed or cut away material from the axial frame members 126, it is not required that the cutouts 180 be formed by removing or cutting away material of the axial frame members 126. Rather, it will be understood by one of ordinary skill in the art that the stent 102 and the axial frame members 126 may be initially formed with the cutouts 180 disposed on the axial frame members 126.

Rather than the axial frame members 126 covering up the arc or bend of the crowns 110 of the inflow portion 108 from which they extend, the cutouts 180 result in a portion of the arc or bend of the crowns 110 of the inflow portion 108 being exposed at the area of transition between a crown 110 of the inflow portion 108 and each axial frame member 126. As a result, the crowns 110 that are attached to an axial frame member 126 have a more similar geometry to the crowns 110 directly adjacent thereto that are not attached to an axial frame member 126 and thus have the full arc or bend thereof exposed.

The cutouts 180 permit the side openings 114 (formed by two pairs of opposing crowns 110 and four struts 112) adjacent to the axial frame members 126 to open or expand more uniformly when the stent 102 is in the expanded configuration as best shown in FIGS. 6 and 9. As a result of cutouts 180, all of the side openings 114 adjacent to the transition portion 124 each have substantially the same circumferential width $W_3$ and are circumferentially symmetric when the stent 102 is in the expanded configuration. Conversely, without cutouts 180, the side openings 114 directly adjacent to the axial frame members 126 do not open circumferentially as wide, or have a circumferential width less than, the side openings 114 that are not directly adjacent to the axial frame members 126. Stated another way, by removing material at the first ends 156, 172 of the axial frame members 126, the side openings 114 adjacent to the axial frame members 126 are permitted to open up further than without the cutouts 180 to result in similar deployment angles, with a deployment angle being defined as the measured angle between struts. The cutouts 180 change the effective length of the struts 112 of the side openings 114 adjacent to the axial frame members 126, which results in all side openings 114 adjacent to the transition portion 124 expanding or opening to substantially the same width $W_3$ when the stent 102 is in the expanded configuration.

In an embodiment, each cutout 180 is substantially semicircular in shape such that the area of transition between a crown of the inflow portion 108 and each axial frame member 126 has an hourglass configuration. The semicircular shape of each cutout 180 results in a portion of the arc or bend of the crowns 110 of the inflow portion 108 being exposed at the area of transition between a crown of the inflow portion 108 and each axial frame member 126 as described above such that the crowns 110 that are attached to an axial frame member 126 have a more similar geometry to the crowns 110 directly adjacent thereto that are not attached to an axial frame member 126. However, the cutouts 180 may be formed in any shape including semicircular, triangular, or rectangular that results in a desired symmetry of the stent 102 in the crimped and expanded configurations. One skilled in the art will realize that other configurations and shapes of the cutouts 180 may provide a benefit for a given application.

Due to the presence of the cutouts 180, the first ends 156, 172 of each axial frame member 126 has a reduced width relative to a width of a remaining length of the axial frame member 126. Stated another way, the reduced width of the first ends 156, 172 of each axial frame member 126 is formed from the pair of cutouts 180 disposed on opposing sides of the first ends 156, 172 of each axial frame member 126. As shown in FIG. 5, the axial frame members 126 have a reduced width $W_2$ at the first ends 156, 172 thereof. The axial frame members 126 have a width $W_1$ along a length thereof between the first ends 156, 172 and the crown 120 of the outflow portion 118. In an embodiment, the reduced width $W_2$ of the first ends 156, 172 is between 60% and 95% of the width $W_1$ of the length of the axial frame member 126 between the first ends 156, 172 and the crowns 120 of the outflow portion 118. In an embodiment, the reduced width $W_2$ of the first ends 156, 172 is between 70% and 90% of the width $W_1$ of the length of the axial frame member 126 between the first ends 156, 172 and the crowns 120 of the outflow portion 118. In an embodiment, the first ends 156, 172 of each axial frame members 126 has a reduced width $W_2$ between 0.60 and 0.70 mm while the length of the axial frame member 126 between the first end 156, 172 and the crown 120 of the outflow portion 118 has a width $W_1$ between 0.70 and 0.85 mm. As used herein, "a length between the first end 156, 172 and the crown 120 of the outflow portion 118" of an axial frame member 126 refers to the length of the axial frame member 126 extending between the cutouts 180 and the crown 120 of the outflow portion 118 that is disposed closer to the inflow end 106 of the stent 102. In an embodiment, a length of each cutout 180 is between 1% and 20% of the length of the axial frame member 126 between the first end 156, 172 and the crown 120 of the outflow portion 118. In an embodiment, a length of each cutout 180 is between 5% and 15% of the length of the axial frame member 126 between the first end 156, 172 and the crown 120 of the outflow portion 118. In an embodiment, each cutout 180 has a length between 0.30 and 0.40 mm while the length of the axial frame member 126 between the first end 156, 172 and the crown 120 of the outflow portion 118 has a length between 2.5 and 3.0 mm.

In the embodiment shown, there is a single row of struts 122 and crowns 120 coupled to the axial frame members 126 and defining the outflow end 116 of the stent 102. Further, in the embodiment shown, exactly two struts 122 and a single crown 120 of the outflow portion 118 are disposed between adjacent axial frame members 126. Such an arrangement provides a series of six endmost outflow side openings or cells 125 formed at the outflow portion 118 of the stent 102. Each endmost outflow side opening or cell 125 defines an open space in the stent 102, which is formed in any type of shape, in the radially expanded configuration. In an embodiment, as best shown in FIG. 8 which is a side view of a single endmost outflow side opening 125 of the stent 102, each endmost outflow side opening 125 is defined by two adjacent struts 122 of the outflow portion 118, four adjacent struts 112 of the inflow portion 108, and two adjacent axial frame members 126 of the transition portion 124. The endmost outflow side openings 125 of the outflow portion 118 are relatively larger than the plurality of side openings 114 of the inflow portion 108 (defined by four adjacent struts 112 of the inflow portion 108) to improve access to the coronary arteries. More particularly, the endmost outflow side openings 125 of the outflow portion 118 are configured to be of sufficient size to be easily crossed with a coronary guide catheter into either the right coronary artery or the left main coronary artery once the transcatheter valve prosthesis 100 is deployed in situ. The inflow portion 108 includes exactly three rows of struts 112 and crowns 110 between the first ends 156, 172 of the axial frame members 126 and the inflow end 106 of the stent 102. Further, four struts 112 and three crowns 110 are disposed between adjacent axial frame members 126.

In another embodiment hereof (not shown), the axial struts 126B of the stent 102 may also be lengthened to include an outflow portion similar to outflow portion 154B of the commissure posts 126A. Lengthening the axial struts 126B in addition to the commissure posts 126A may aid in valve alignment and coaptation. Further, although the commissure posts 126A are described herein as lengthened relative to the axial struts 126B, in another embodiment hereof the commissure posts 126A may have the same length as the axial struts 126B such that they do not include an outflow portion.

Figure 12:
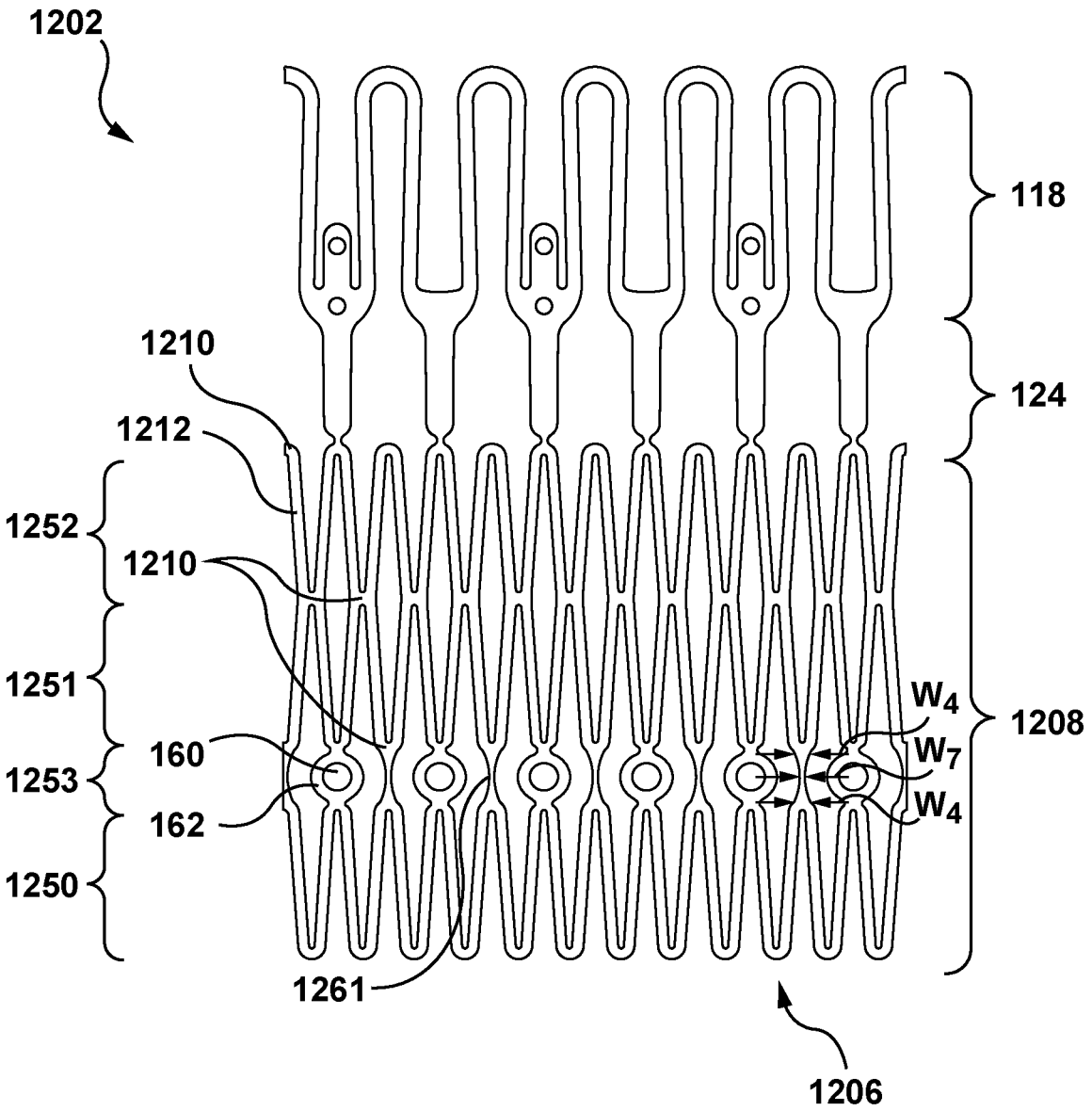
FIG. 12 is a side view of a stent of a transcatheter valve prosthesis according to another embodiment hereof, wherein the stent is in the non-expanded or crimped configuration and has been laid flat for illustrative purposes only.

FIG. 12 is a side view of a stent 1202 according to another embodiment hereof. In FIG. 12, the stent 1202 is in a non-expanded or crimped configuration and is laid flat for illustrative purposes only. The stent 1202 is similar to the stent 102 except as described herein. More particularly, the stent 1202 may be balloon-expandable and includes an inflow portion 1208, the outflow portion 118, and the transition portion 124 bridging, connecting, or otherwise extending between the inflow portion 1208 and the outflow portion 118. As illustrated in FIG. 12, the inflow portion 1208 of the stent 102 can include three rows of the struts 1212: a first row 1250 of the struts 1212 formed proximate to an inflow end 1206, a second row 1251 of the struts 1212 formed between the first row 1251 and a third row 1252, and the third row 1252 of struts 1212 formed proximate to the transition portion 124. Similar to the stent 102, the plurality of inflow markers 160 is positioned at the intersection 1253 of the first row 1250 and the second row 1251. The inflow markers 160 are positioned at every other intersection of a pair of the struts 1212 of the first row 1250 and a pair of the struts 1212 of the second row 1251. Each inflow marker 160 is attached to the stent 102 within a containment member 162, which is configured as a hollow structure or opening in the stent 1202 which can receive the inflow marker 160. When a marker 160 is not present, an axial extension 1261 is disposed at the intersection 1253, between a pair of the struts 1212 of the first row 1250 and a pair of the struts 1212 of the second row 1251. Thus, the inflow portion 1208 may be considered to include a plurality of containment members 162 and a plurality of axial extensions 1261, with an axial extension 1261 disposed between a pair of adjacent containment members 162. The axial extensions 1261 extend substantially parallel to the longitudinal axis LA of the stent 1202. Each axial extension 1261 extends between a first crown 1210 of the inflow portion 1208 and a second crown 1210 of the inflow portion 1208, with a first transition area extending between a first end of the axial extension 1261 and the first crown 1210 and a second transition area extending between a second end of the axial extension 1261 and the second crown 1210. At the areas of transition between the first and second crowns 1210 of the inflow portion 1208 and the axial extension 1261, each area of transition has a width $W_4$ as shown in FIG. 12 similar to the axial extensions 161 described above.

The inflow portion 1208 differs from the inflow portion 108 at the intersection 1253 in the following manner. For the stent 102, the axial extensions 161 have a constant or uniform width $W_6$ along a length thereof as shown and described with respect to FIG. 4 herein. However, in the stent 1202, the axial extensions 1261 have a varying or non-uniform width along a length thereof. More particularly, along a length of each axial extension 1261 from a first end to a second end thereof, each axial extension 1261 has a width that gradually and consistently tapers to a midportion thereof that has a reduced width $W_7$ (which is relatively less than the width $W_6$ of the axial extension 161). Stated another way, each axial extensions 1261 has a varying or non-uniform width along a length thereof such that a midportion thereof is relatively narrower than the first and second ends thereof. This slimming effect of the axial extensions 1261 results in a reduced profile of the stent 1202 when in the crimped or non-expanded configuration. In an embodiment, the reduced width $W_7$ is between 40% and 60% of width $W_4$.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A prosthesis comprising:
a stent having a crimped configuration for delivery within a vasculature and an expanded configuration for deployment within a native heart valve, the stent including:
a plurality of axial frame members,
an inflow portion including at least three rows of struts and crowns formed between adjacent pairs of the struts, wherein the at least three rows of the inflow portion are formed between an inflow end of the axial frame members and an inflow end of the stent, and
an outflow portion formed proximate to an outflow end of the stent and including a single row of struts and crowns formed between adjacent pair of the struts, the outflow portion being coupled to an outflow end of the axial frame members, wherein exactly two struts of the plurality of struts of the outflow portion are disposed between adjacent axial frame members,
wherein each axial frame member extends in an axial direction along a longitudinal axis of the stent from a crown of the inflow portion to at least a crown of the outflow portion, each axial frame member having a first end adjacent to a crown of the inflow portion, the first end having a reduced width relative to a width of a length of the axial frame member between the first end and the crown of the outflow portion, and
wherein the reduced width of the first end of each axial frame member is formed from a pair of cutouts disposed on opposing sides of the first end of each axial frame member and a length of each cutout is between 1% and 20% of the length of the axial frame member between the first end and the crown of the outflow portion, the pair of cutouts resulting in a curved portion of the crown of the inflow portion being exposed at an area of transition between the crown of the inflow portion and the axial frame member.

2. The prosthesis of claim 1, wherein the plurality of axial frame members includes exactly six axial frame members, wherein three of the six axial frame members are commissure posts and three of the six axial frame members are axial struts, and wherein each of the axial struts is disposed between adjacent commissure posts.

3. The prosthesis of claim 1, wherein endmost inflow crowns are formed at the inflow end of the stent and wherein endmost outflow crowns are formed at the outflow end of the stent, and wherein a total of the endmost inflow crowns are greater than a total of the endmost outflow crowns.

4. The prosthesis of claim 1, wherein a first diameter of the inflow end of the stent and a second diameter of the outflow end of the stent are substantially similar.

5. The prosthesis of claim 1, wherein the reduced width of the first end of each axial frame member is between 70% and 90% of the width of the length of the axial frame member between the first end and the crown of the outflow portion.

6. The prosthesis of claim 1, wherein each cutout of the pair of cutouts is semicircular.

7. The prosthesis of claim 1, further comprising:

the inflow portion having a plurality of containment members and a plurality of axial extensions, with an axial extension disposed between a pair of adjacent containment members, wherein each containment member is configured to hold a radiopaque maker and each axial extension extends substantially parallel to the longitudinal axis of the stent; and wherein each axial extension extends between a first crown of the inflow portion and a second crown of the inflow portion, with a first transition area extending between a first end of the axial extension and the first crown and a second transition area extending between a second end of the axial extension and the second crown, and wherein a first junction extends between a third crown of the inflow portion and the containment member and a second junction extends between a fourth crown of the inflow portion and the containment member, and wherein a first width of the first and second transition areas is between 75% and 99% of a second width of the first and second junctions.

8. The prosthesis of claim 1, wherein the length of each cutout is between 5% and 15% of the length of the axial frame member between the first end and the crown of the outflow portion.

9. The prosthesis of claim 1, wherein the at least three rows of struts and crowns formed between adjacent pairs of the struts of the inflow portion form a plurality of side openings and the side openings that are adjacent to the plurality of axial frame members are substantially equal in circumferential width when the stent is in the expanded configuration.

10. The prosthesis of claim 1, wherein the plurality of axial frame members includes three commissure posts and each commissure post has a second end opposing the first end, the second end being unattached and disposed within the outflow portion.

11. A transcatheter valve comprising:

An expandable stent including:

An inflow portion (including an alternating structure of crowns and struts);

An outflow portion (including an alternating structure of crowns and struts);

A plurality of axial frame members, each axial frame member extending along a longitudinal direction of the stent from a first end at crown of the inflow portion to at least a crown of the outflow portion, the width at the first end is reduced (with a pair of cut outs on opposing sides thereof) in comparison to the width of a length of the axial frame member between the first end and the crown of the outflow portion, the length of each cut out is such a specific portion (1-20%) of the length of the axial frame member between the first end and the crown of the outflow portion, the pair of cuts being positioned such that a curved portion of the crown of the inflow portion is exposed between the crown of the inflow portion and the axial frame member, A prosthetic valve secured to at least one of the axial frame members;

With respect to claim 9:

A prosthesis comprising:

An expandable stent including:

A plurality of axial frame members;

An inflow portion (including at least three rows of crowns and struts);

An outflow portion (including a single rows of crowns and struts), the outflow portion attached to the axial frame members such that there are exactly two struts between a pair of axial frame members;

each axial frame member extending along a longitudinal direction of the stent from a first end at crown of the inflow portion to at least a crown of the outflow portion, the width at the first end is reduced (with a pair of cut outs on opposing sides thereof) in comparison to the width of a length of the axial frame member between the first end and the crown of the outflow portion, the length of each cut out is such a specific portion (1-20%) of the length of the axial frame member between the first end and the crown of the outflow portion, the pair of cuts being positioned such that a curved portion of the crown of the inflow portion is exposed between the crown of the inflow portion and the axial frame member.

12. The transcatheter valve prosthesis of claim 11, wherein the reduced width of the first end of each axial frame member is between 60% and 95% of the width of the length of the axial frame member between the first end and the crown of the outflow portion.

13. The transcatheter valve prosthesis of claim 11, wherein each cutout of the pair of cutouts is semicircular.

14. The transcatheter valve prosthesis of claim 11, wherein endmost inflow crowns are formed at the inflow end of the stent and wherein a total of the endmost inflow crowns are greater than a total of the endmost outflow crowns.

15. The transcatheter valve prosthesis of claim 11, wherein a first diameter of the inflow end of the stent and a second diameter of the outflow end of the stent are substantially similar.

16. The transcatheter valve prosthesis of claim 11, further comprising:

the prosthetic valve including three leaflets and three commissures, each commissure being formed by attached adjacent lateral ends of an adjoining pair of the three leaflets; and wherein the plurality of axial frame members includes a total of six axial frame members, and wherein three of the six axial frame members are aligned with and attached to a respective commissure of the three leaflets of the prosthetic valve.

17. The transcatheter valve prosthesis of claim 11, further comprising:

the inflow portion having a plurality of containment members and a plurality of axial extensions, with an axial extension disposed between a pair of adjacent containment members, wherein each containment member is configured to hold a radiopaque maker and each axial extension extends substantially parallel to the longitudinal axis of the stent; and wherein each axial extension extends between a first crown of the inflow portion and a second crown of the inflow portion, with a first transition area extending between a first end of the axial extension and the first crown and a second transition area extending between a second end of the axial extension and the second crown, and wherein a first junction extends between a third crown of the inflow portion and the containment member and a second junction extends between a fourth crown of the inflow portion and the containment member, and wherein a first width of the first and second transition areas is between 75% and 99% of a second width of the first and second junctions.

18. The transcatheter valve prosthesis of claim 11, wherein the length of each cutout is between 5% and 15% of the length of the axial frame member between the first end and the crown of the outflow portion.

19. The transcatheter valve prosthesis of claim 11, wherein the side openings of the inflow portion that are adjacent to the plurality of axial frame members are substantially equal in circumferential width when the stent is in the expanded configuration.

20. The transcatheter valve prosthesis of claim 11, wherein the plurality of axial frame members includes three commissure posts and each commissure post has a second end opposing the first end, the second end being unattached and disposed within the outflow portion.

* * * * *